(12) United States Patent
Wang

(10) Patent No.: US 10,792,122 B2
(45) Date of Patent: Oct. 6, 2020

(54) OBJECT DEVELOPING AND CALIBRATING METHOD IN A SURGICAL ENVIRONMENT

(71) Applicant: TAIWAN MAIN ORTHOPAEDIC BIOTECHNOLOGY CO., LTD., Taichung (TW)

(72) Inventor: Min-Liang Wang, Taichung (TW)

(73) Assignee: TAIWAN MAIN ORTHOPAEDIC BIOTECHNOLOGY CO., LTD., Taichung (TW)

(*) Notice: Subject to any disclaimer, the term of this patent is extended or adjusted under 35 U.S.C. 154(b) by 33 days.

(21) Appl. No.: 16/231,513

(22) Filed: Dec. 23, 2018

(65) Prior Publication Data

US 2020/0197123 A1    Jun. 25, 2020

(51) Int. Cl.
| | | |
|---|---|---|
| *G09G 5/00* | (2006.01) | |
| *A61B 90/35* | (2016.01) | |
| *A61B 90/00* | (2016.01) | |
| *A61B 34/00* | (2016.01) | |
| *A61B 34/10* | (2016.01) | |
| *A61B 34/30* | (2016.01) | |
| *A61B 34/20* | (2016.01) | |
| *A61B 90/50* | (2016.01) | |

(52) U.S. Cl.
CPC .............. *A61B 90/35* (2016.02); *A61B 34/10* (2016.02); *A61B 34/25* (2016.02); *A61B 90/361* (2016.02); *A61B 90/37* (2016.02); *A61B 34/30* (2016.02); *A61B 2034/207* (2016.02); *A61B 2034/2055* (2016.02); *A61B 2090/365* (2016.02); *A61B 2090/368* (2016.02); *A61B 2090/3612* (2016.02); *A61B 2090/374* (2016.02); *A61B 2090/378* (2016.02); *A61B 2090/3735* (2016.02); *A61B 2090/502* (2016.02)

(58) Field of Classification Search
CPC ............ A61B 34/20; A61B 2034/2055; A61B 2090/374; A61B 2090/371; A61B 6/4441; A61B 34/25; G06T 7/55; G06T 7/70; G02B 27/0172; G06F 3/0482
USPC .................................................. 345/204, 7–8
See application file for complete search history.

(56) References Cited

U.S. PATENT DOCUMENTS

| 2018/0081179 A1* | 3/2018 | Samec .................. G06F 3/0304 |
| 2019/0117318 A1* | 4/2019 | Charron ................ A61B 34/20 |

* cited by examiner

*Primary Examiner* — Jennifer T Nguyen
(74) *Attorney, Agent, or Firm* — Pai Patent & Trademark Law Firm; Chao-Chang David Pai

(57) ABSTRACT

The invention discloses an object developing and calibrating method in a surgical environment. The method mainly includes the steps of: using at least one infrared LED (IR-LED) and at least one infrared sensor (IR-Sensor) on a surgical eyeglass, to have a surgical environment image; and retaining image signals within a first wavelength range and removing image signals not in the first wavelength range in the surgical environment image. The method helps the surgeon see only the object images on the surgical eyeglass without the interference of non-surgical environmental imaging noises.

10 Claims, 5 Drawing Sheets

Step 3.1: emitting an infrared signal from the infrared LED on the surgical eyeglass to illuminate a calibration device and the surgical instrument

Step 3.2: receiving the infrared signal reflected by the reflective IR coating on the calibration device and the surgical instrument by the infrared sensor on the surgical eyeglass and then transmitting the reflected infrared signal to the image processing module of the computer

FIG. 4

OBJECT DEVELOPING AND CALIBRATING METHOD IN A SURGICAL ENVIRONMENT

BACKGROUND OF THE INVENTION

1. Field of the Invention

The present invention relates to a surgical assistance method, and more particularly to an object developing and calibrating method in a surgical environment, that can exclude the images of other incoherent objects in the surgical environment from the surgical eyeglass.

2. Description of the Related Art

In recent years, with the development of new health care technology, the use of computer-assisted surgery has increased significantly. Since the accuracy of surgical instruments and imaging technology has improved, doctors not only can enhance the quality of their surgery, but also can minimize patient wounds caused by surgery. Generally, a computer-assisted surgery consists of four parts: acquiring images from a patient, image analysis and processing, pre-diagnosis and surgical planning simulation, and finally receiving the surgery guidance for the patient. Computer-assisted surgery of the surgery currently is divided into the following steps: (1) using tomography images, including computerized tomography (CT), magnetic resonance imaging (MRI), X ray, nuclear medicine imaging, reconstructed 3D models (non-real-time image); and (2) using the mobile C-arm X-ray machine or ultrasound imaging in the operating room as an auxiliary guide (real-time image) and a non-image-based guidance system.

Clinical application of image guided surgical systems includes spinal surgery guide (e.g., pedicle screw fixation, removal of damaged sites, removal of lumps, and disposing electrode to a fixed depth for epilepsy patients); head lesion surgery (e.g., treatment of meningioma, craniopharyngioma, chondrosarcoma, and other lesions in the cranial portion); tumor resection tissue sections; treatment of Parkinson's disease; treatment of huibu brain stereotaxic of psychiatric disorders; audition functional sinus surgery; neurovascular surgical repair and ventricular bypass surgery and ventricular shunt replacement surgery. This system can also be used for the hip and knee surgery, such as total knee arthroplasty, total hip replacement surgery, and anterior cruciate ligament reconstruction.

Operation must be combined with image guide, electronic, machinery, and other techniques, so the orientation of the surgical instrument projected onto the image may assist a physician to grasp the relative orientation between the device and the patient and to achieve the purpose of navigation. Before the operation, the doctor first puts a mark on the patient's surgical position, and then allows the patient to undergo a computerized tomography or magnetic resonance imaging examination. The image of computerized tomography or magnetic resonance image is reconstructed in the computer to form the three-dimensional position near the surgical site, and the location of the anomaly and normal functional area are indicated. At the time of surgery, surgical site of the patient and the surgical instruments have mounting marks, and then infrared camera (ultrasound or the like) can label the location and relative positions of the surgical site and the surgical instrument simultaneously to create space surgery relationship according to these infrared signals reflected from the mark. In addition, the surgeon may use the head or heads-up display through the eyepiece to see the image reorganization.

Augmented Reality (Augmented Reality, AR) and Mixed Reality (Mixed Reality, MR) are generally used to display virtual information on the real image of the patient. Particularly in minimally invasive surgery using the endoscope in the past, the overlay of images is performed in the augmented and mixed reality images. The images in the minimally invasive surgery can not be directly observed by the camera, but now the image can be seen prior to surgery. Augmented and mixed reality assist the surgeon to see through the patient's body part, so that the doctor prior to the surgical site visits, vital structures thereof can be effectively positioned without confirming the position beforehand by performing the operation. Augmented and mixed reality technology seems to be currently the most promising research, which helps guide the surgeon and process supervision robotic surgery.

However, when surgeons use surgical eyeglass with stereoscopic visualization for medical procedures, non-surgical environmental imaging noises in the surgical environment, such as operating table, or drop rack, can interfere with the surgeon's image judgments of the surgical instruments.

In view of the above problems, it is necessary to propose an object developing and calibrating method in a surgical environment. The images of other incoherent objects in the surgical environment are excluded from the surgical eyeglass. The objects seen on the surgical eyeglass retain only the images that the surgeon intends to look at, such as images of surgical instruments, affected areas, etc.

BRIEF SUMMARY OF THE INVENTION

An object of the present invention is to provide an object developing and calibrating method in a surgical environment, to solve the problem of the interference of non-surgical environmental imaging noises in the surgical environment, such as operating table, or drop rack, and thus to help the surgeon see the object images that the surgeon intends to look at on the surgical eyeglass such as the images of surgical instruments, affected areas, etc.

In order to achieve the above object, the present invention discloses an object developing and calibrating method in a surgical environment, comprising the following steps of:

Step 1: disposing at least one infrared light emitting diode (IR-LED) and at least one infrared sensor (IR-Sensor) on a surgical eyeglass, the infrared LED emitting an infrared signal to illuminate a plurality of objects of the surgical environment, and the infrared sensor receiving the infrared signal reflected by the plurality of objects to form an object image of the surgical environment;

Step 2: transmitting the object image of the surgical environment to an image processing module of a processing device such as computer, workstation and processing board etc.;

Step 3: forming a spatial variation image for a displacement of the surgical instrument by the at least one infrared light-emitting diode and the at least one infrared sensor on the surgical eyeglass;

Step 4: transmitting the spatial variation image to the image processing module of the computer to overlap with the object image of the surgical environment to form a surgical environment image; and Step 5: with the image processing module of the computer, retaining image signals within a first wavelength range in the surgical environment image and removing image signals not in the first wavelength range.

According to one aspect of the present invention, the step 3 further comprises the following steps:

Step 3.1: emitting an infrared signal from the infrared LED on the surgical eyeglass to illuminate a calibration device and the surgical instrument, the calibration device having a plurality of geometric patterns on the calibration device, and having a reflective IR coating outside the geometric patterns of the calibration device, and a specific point on the surgical instrument also having a reflective IR coating, to reflect the infrared signal; and Step 3.2: receiving the infrared signal reflected by the reflective IR coating on the calibration device and the surgical instrument by the infrared sensor on the surgical eyeglass and then transmitting the reflected infrared signal to the image processing module of the computer to form a spatial variation image.

According to one aspect of the present invention, the step 3.2 further comprises the following steps:

Step 3.2.1: setting with a plurality of geometric patterns on the calibration device;

Step 3.2.2: finding the center point of each geometric pattern on the calibration device;

Step 3.2.3: defining the center point of one of the geometric patterns on the calibration device as a first reference calibration point;

Step 3.2.4: by using the first reference calibration point as a positioning reference point, finding the distance between the center point of each other geometric pattern on the calibration device and the first reference calibration point to make a translation matrix formula;

Step 3.2.5: placing the surgical instrument to be used at any position above the calibration device to define a second reference calibration point; and Step 3.2.6: using the translation matrix formula to generate spatial variation image for the shift of the surgical instrument.

According to one aspect of the present invention, the reflective IR coating are made with pigments and an organic or inorganic vehicle.

According to one aspect of the present invention, the geometric patterns are selected from circular patterns or triangular patterns or another known geometrical object.

According to one aspect of the present invention, the geometric patterns have a distance between 0.2 mm and 0.5 mm.

According to one aspect of the present invention, a wavelength of the infrared signal emitted by the at least one infrared LED is in the range of 750 nm to 1100 nm.

According to one aspect of the present invention, a wavelength of the infrared signal received by the at least one infrared sensor is in the range of 750 nm to 1100 nm.

According to one aspect of the present invention, the image signal in the first wavelength range is an image signal having a wavelength of 750 nm to 1100 nm.

According to one aspect of the present invention, in step 4: the spatial variation image and the object image of the surgical environment is overlapped by an image overlay software in the image processing module of the computer.

BRIEF DESCRIPTION OF THE DRAWINGS

FIG. 4 is a procedure flowchart of an embodiment of the object developing and calibrating method of the present invention.

DETAILED DESCRIPTION OF THE INVENTION

While the present invention can be applied in different forms of embodiment, the drawings and the following description are merely of preferred embodiments of the present invention by way of examples, and are not intended to limit the invention to the illustrated and/or described in any particular embodiment.

The present invention provides an object developing and calibrating method that can be applied to computer-assisted glasses with enhanced authenticity for surgery (namely, augmented and mixed reality computer assisted glasses for surgical operation). The enhanced authenticity can be seen as a mixture of virtual and real-world space that synchronizes patient information.

The surgical eyeglass may be saved in a patient database. In addition, the image overlay software may be operable to create and transmit laboratory prescriptions, such as digital models of anatomical features, or applicable to an on-site or off-site laboratory for use in fabricating a prosthetic (e.g., partial dentures, implant abutments, orthodontic appliances, and the like), surgical guides, or the like OOOPDS (object-oriented orthopedic surgery) software.

Figure 1:
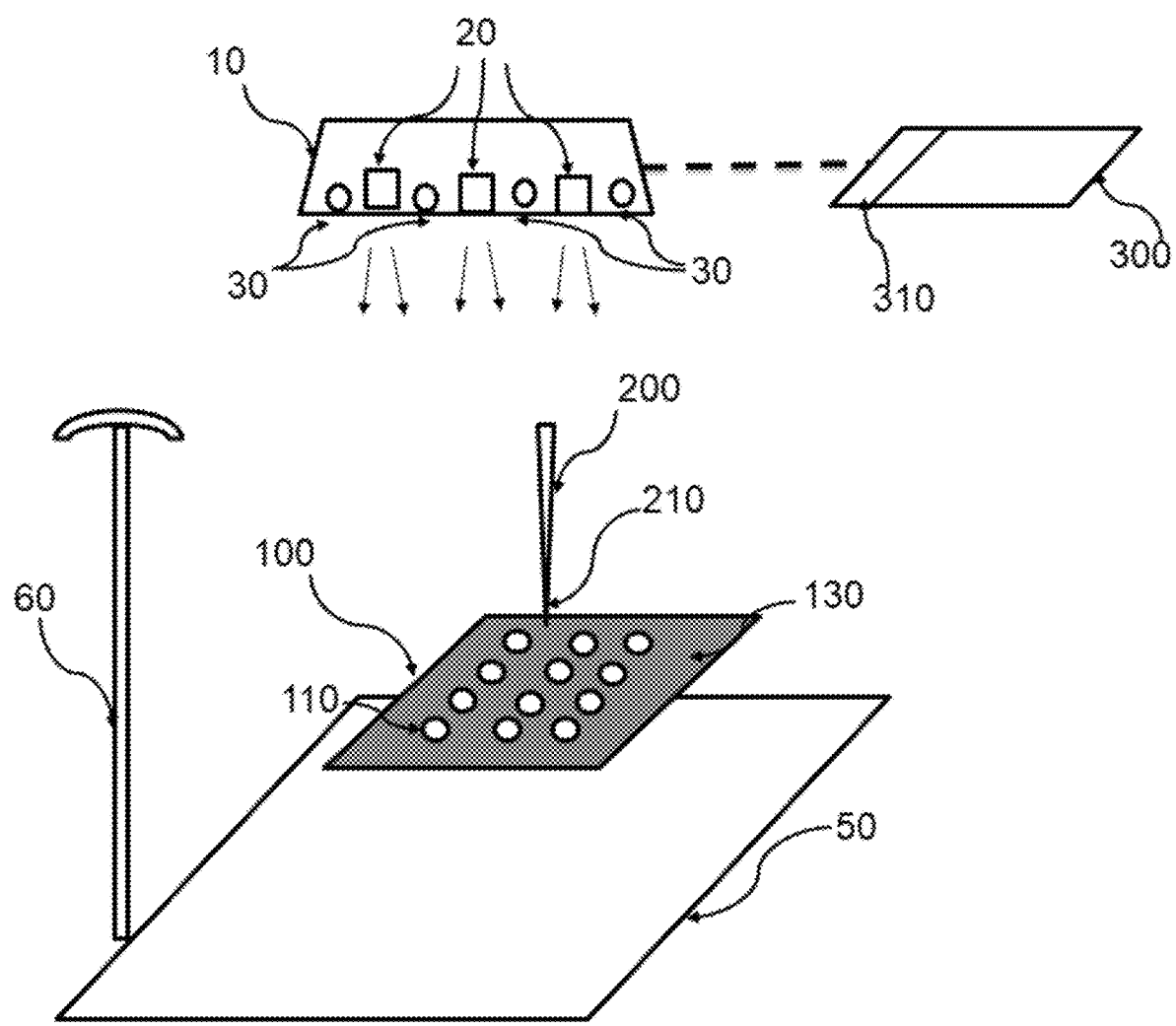
FIG. 1 is a schematic diagram of a plurality of objects of the surgical environment.
Figure 2:
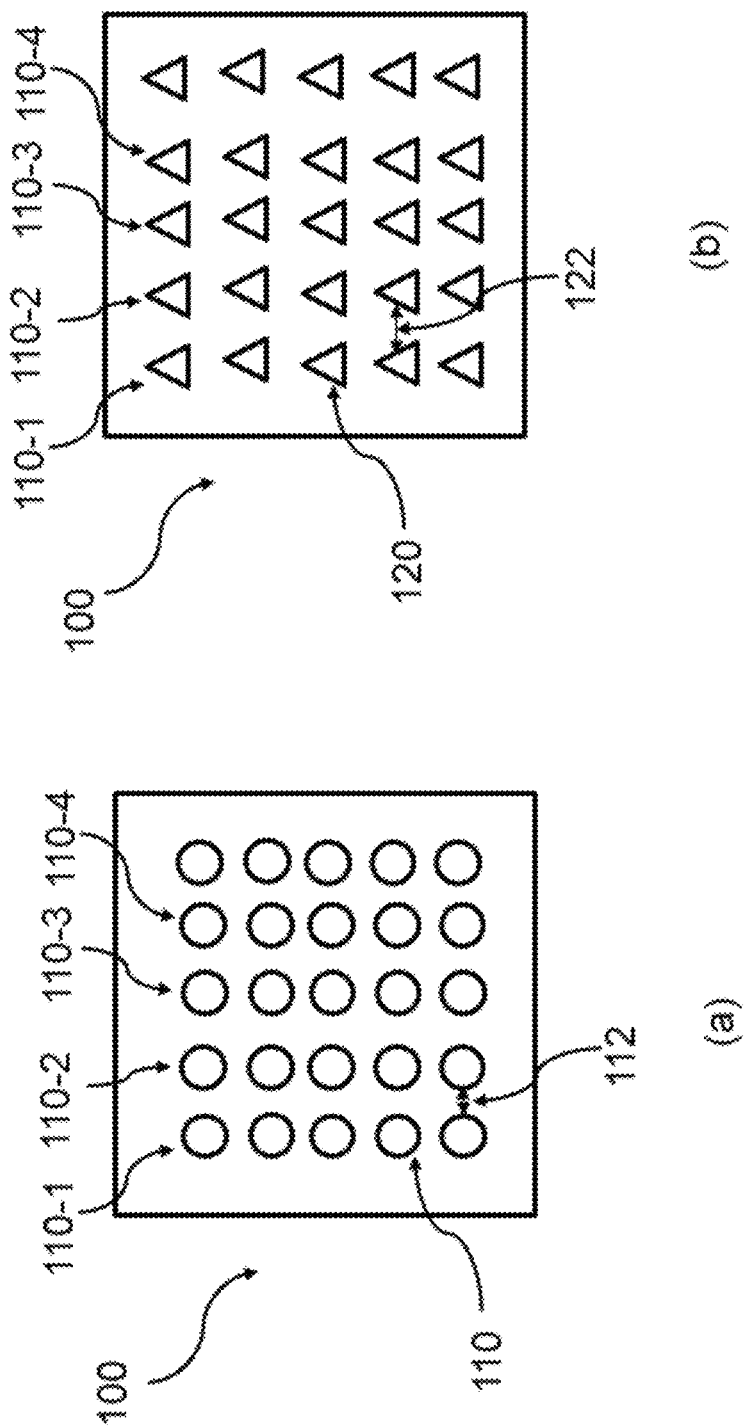
FIG. 2 is a schematic diagram of a plurality of geometric patterns using (a) circular patterns and (b) triangular patterns on the calibration device.

FIG. 1 shows a schematic diagram of a plurality of objects of the surgical environment. Also referring to FIG. 2, it is a schematic diagram of a plurality of geometric patterns using (a) circular patterns and (b) triangular patterns on the calibration device such as the calibration plate or the calibration tool. In an embodiment, the geometric patterns can be formed on the calibration plate by, for example, drawing or depositing some color. The distance of the geometric patterns is defined as the distance between the centers of the two immediately adjacent geometric patterns. A distance ratio of the geometric is defined as the ratio of the distances between the (n+2)th geometric pattern and (n+1)th geometric pattern to the distances between the (n+1)th geometric pattern and nth geometric pattern. In an embodiment, the distance ratio of the geometric patterns is set as a same value. For example, the distance ratio is equal to 1. Namely, the distances between the first geometric pattern 110-1 and second geometric pattern 110-2 is 0.1 mm, the distances between the second geometric pattern 110-2 and third geometric pattern 110-3 is 0.1 mm, and the distances between the third geometric pattern 110-3 and fourth geometric pattern 110-4 is 0.1 mm. Another, the distance ratio is equal to 2. Namely, the distances between the first geometric pattern 110-1 and second geometric pattern 110-2 is 0.1 mm, the distances between the second geometric pattern 110-2 and third geometric pattern 110-3 is 0.2 mm, and the distances between the third geometric pattern 110-3 and fourth geometric pattern 110-4 is 0.4 mm. As shown in FIG. 2, the geometric patterns have a distance 112, 122 between 0.1 mm and 1 mm. In a preferred embodiment, the distance of adjacent geometric patterns is between 0.2 mm and 0.5 mm, thus the distance is small enough to have accurate calibration.

In the surgical environment, there are many objects, comprising a surgical eyeglass 10 disposed with at least one infrared LED (IR-LED) 20 and at least one infrared sensor (IR-Sensor) 30, a processing device 300 with an image processing module 310, a calibration device 100 having a plurality of geometric patterns 110 or 120, and a reflective IR coating 130 outside the geometric patterns 110 or 120, and a surgical instrument 200 with a specific point 210 having a reflective IR coating, an operating table 50, or drop rack 60.

In this invention, the present invention is to provide an object developing and calibrating method in a surgical environment, to solve the problem of the interference of non-surgical environmental imaging noises in the surgical environment, such as operating table 50, or drop rack 60, but not limited thereto, and thus to help the surgeon see the object images that the surgeon intends to look at on the surgical eyeglass 10, such as the images of surgical instruments 200, affected areas, etc.

Figure 3:
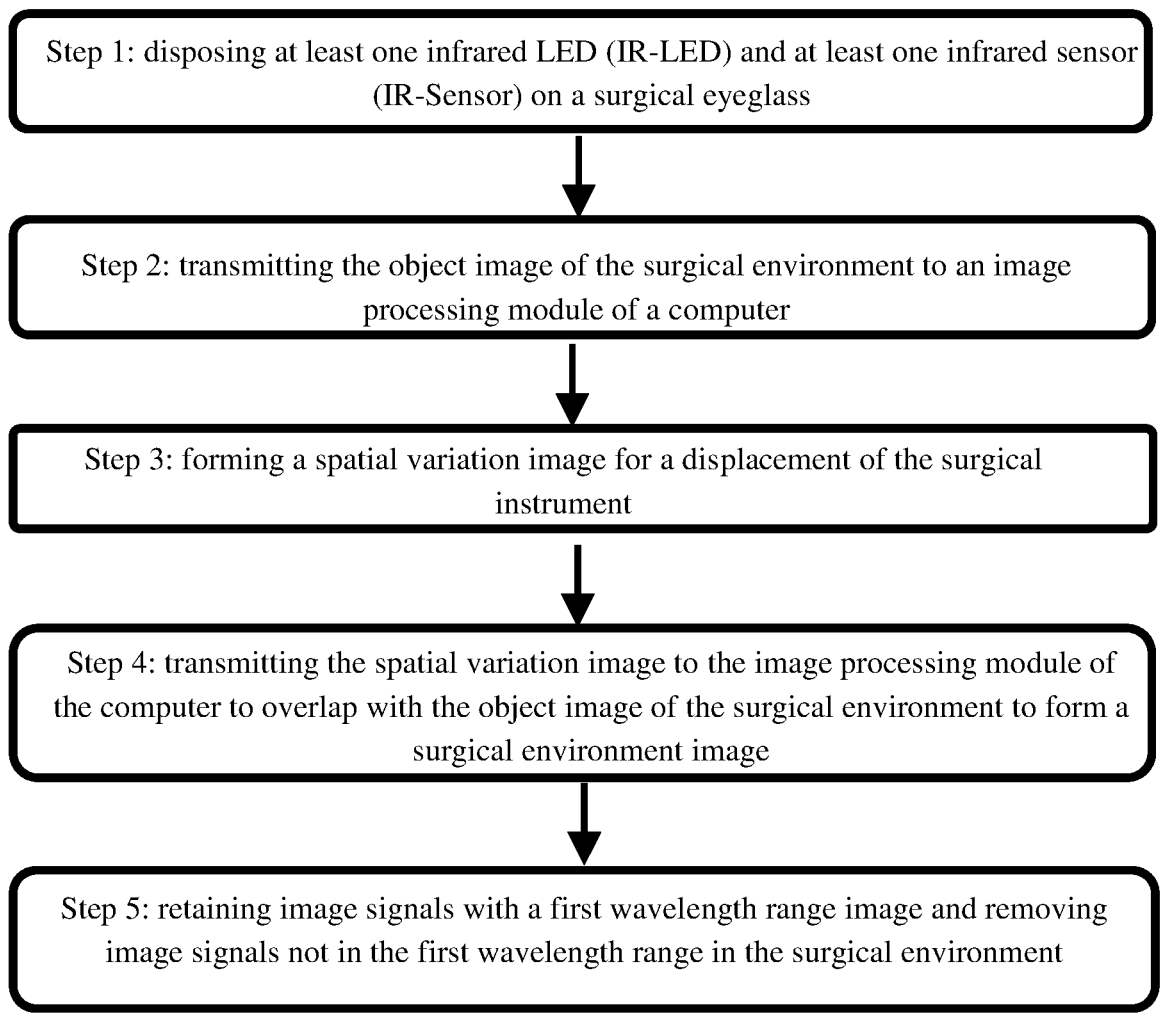
FIG. 3 is a procedure flowchart of the object developing and calibrating method of the present invention.

FIG. 3 shows a procedure flowchart of the object developing and calibrating method of the present invention. The object developing and calibrating method in a surgical environment, comprises the following steps of:

Step 1: disposing at least one infrared LED (IR-LED) 20 and at least one infrared sensor (IR-Sensor) 30 on a surgical eyeglass 10, the infrared LED 20 emitting an infrared signal to illuminate a plurality of objects of the surgical environment, and the infrared sensor 30 receiving the infrared signal reflected by the plurality of objects to form an object image of the surgical environment;

Step 2: transmitting the object image of the surgical environment to an image processing module 310 of a processing device 300, such as a computer, workstation and processing board, etc.;

Step 3: forming a spatial variation image for a displacement of the surgical instrument 200 by the at least one IR-LED 20 and the at least one IR-Sensor 30 on the surgical eyeglass 10;

Step 4: transmitting the spatial variation image to the image processing module 310 of the processing device 300 to overlap with the object image of the surgical environment to form a surgical environment image; and Step 5: with the image processing module 310 of the processing device 300, retaining image signals within a first wavelength range in the surgical environment image and removing image signals not in the first wavelength range.

It is known that the image processing module 310 of the processing device 300 which retains image signals within a first wavelength range in the surgical environment image and removes image signals not in the first wavelength range shall at least have an optical filter. The processing device 300 is selected from a computer, a workstation and a processing board, etc. In an embodiment, the surgical eyeglass 10 has also at least an optical filter. The optical filter is a device that selectively transmits light of different wavelengths, and is usually implemented as a glass plane or plastic device in the optical path, which are either dyed in the bulk or have interference coatings. The optical properties of filters are completely described by their frequency response, which specifies how the magnitude and phase of each frequency component of an incoming signal is modified by the filter. Filters mostly belong to one of two categories. The simplest, physically speaking, is the absorptive filter; then there are interference or dichroic filters. In an embodiment, the image signal in the first wavelength range is an image signal having a wavelength of 750 nm to 1100 nm. Namely, the optical filter in the surgical eyeglass 10 or in the processing device 300 has a passband in the wavelength range of 750 nm to 1100 nm.

In an embodiment, a wavelength of the infrared signal emitted by the at least one IR-LED is in the range of 750 nm to 1100 nm, and a wavelength of the infrared signal received by the at least one IR-sensor is in the range of 750 nm to 1100 nm.

In an embodiment, in step 4: the spatial variation image and the object image of the surgical environment is overlapped by an image overlay software in the image processing module 310 of the processing device 300.

The processing device 300 operates the image overlay software for processing images and data, and for communicating images and data via wired or wireless connections. For example, the image overlay software can be used by the medical clinician to manipulate, convert, and overlay images collected by the surgical site image required to be used in other surgical procedures. Although different machines may produce images in different formats, it is desirable that the image overlay software be capable of converting one or more image formats into one or more different formats, so that the images collected by different devices can be displayed together in an overlying fashion. Thus, the image overlay software is configured to access, display, convert, and manipulate a new spatial variation image by combining the spatial variation image with the image of the surgical site to be used in other surgical procedures in various formats including, for example, DICOM (Digital Imaging and Communications in Medicine) images, CAD (Computer Aided Design) images, STL (Standard Template Library) images, or the like. The image overlay software permits a clinician to review digital images, visualize virtual models and create image overlays on a display of the surgical eyeglass worn by a surgeon.

The image overlay software is operable to create and transmit laboratory prescriptions, such as digital models of anatomical features, to an on-site or off-site laboratory for use in fabricating a prosthetic (e.g., partial dentures, implant abutments, orthodontic appliances, and the like), surgical guides, or the like. Images overlay software such as OOPDS 3D medical software is capable of superimposing or overlaying images.

Moreover, in the invention, the method further comprises Step 6: transmitting the image signals within a first wavelength range in the surgical environment image from the image processing module 310 to the surgical eyeglass 10. Then, the objects seen on the surgical eyeglass 10 retain only the images that the surgeon intends to look at, such as images of surgical instruments, affected areas, etc.

FIG. 4 shows a procedure flowchart of an embodiment of the object developing and calibrating method of the present invention. And please also refer to FIG. 2. The step 3 comprises the following steps:

Step 3.1: emitting an infrared signal from the infrared LED 20 on the surgical eyeglass 10 to illuminate a calibration device 100 and the surgical instrument 200, the calibration device 100 having a plurality of geometric patterns 110 and 120 on the calibration device 100, and having a reflective IR coating 130 outside the geometric patterns 110/120 of the calibration device 100, and a specific point 210 on the surgical instrument 200 also having a reflective IR coating, to reflect the infrared signal; and Step 3.2: receiving the infrared signal reflected by the reflective IR coating on the calibration device 100 and the surgical instrument 200 by the infrared sensor 30 on the surgical eyeglass 10 and then transmitting the reflected infrared signal to the image processing module 310 of the processing device 300 to form a spatial variation image.

It is noted that the device coated with the reflective IR coating on the surface of the device reflects the infrared signal from the infrared LED 20. Normal the reflective IR coating are made with pigments and an organic or inorganic vehicle. Titanium dioxide, with high refractive indices for visible and infrared wavelengths, is an excellent material for reflecting the infrared signal. In an embodiment, normal titanium dioxide ($TiO_2$) pigments, while designed to scatter or reflect the infrared signal, have been found to also strongly scatter or reflect NIR light.

Figure 5:
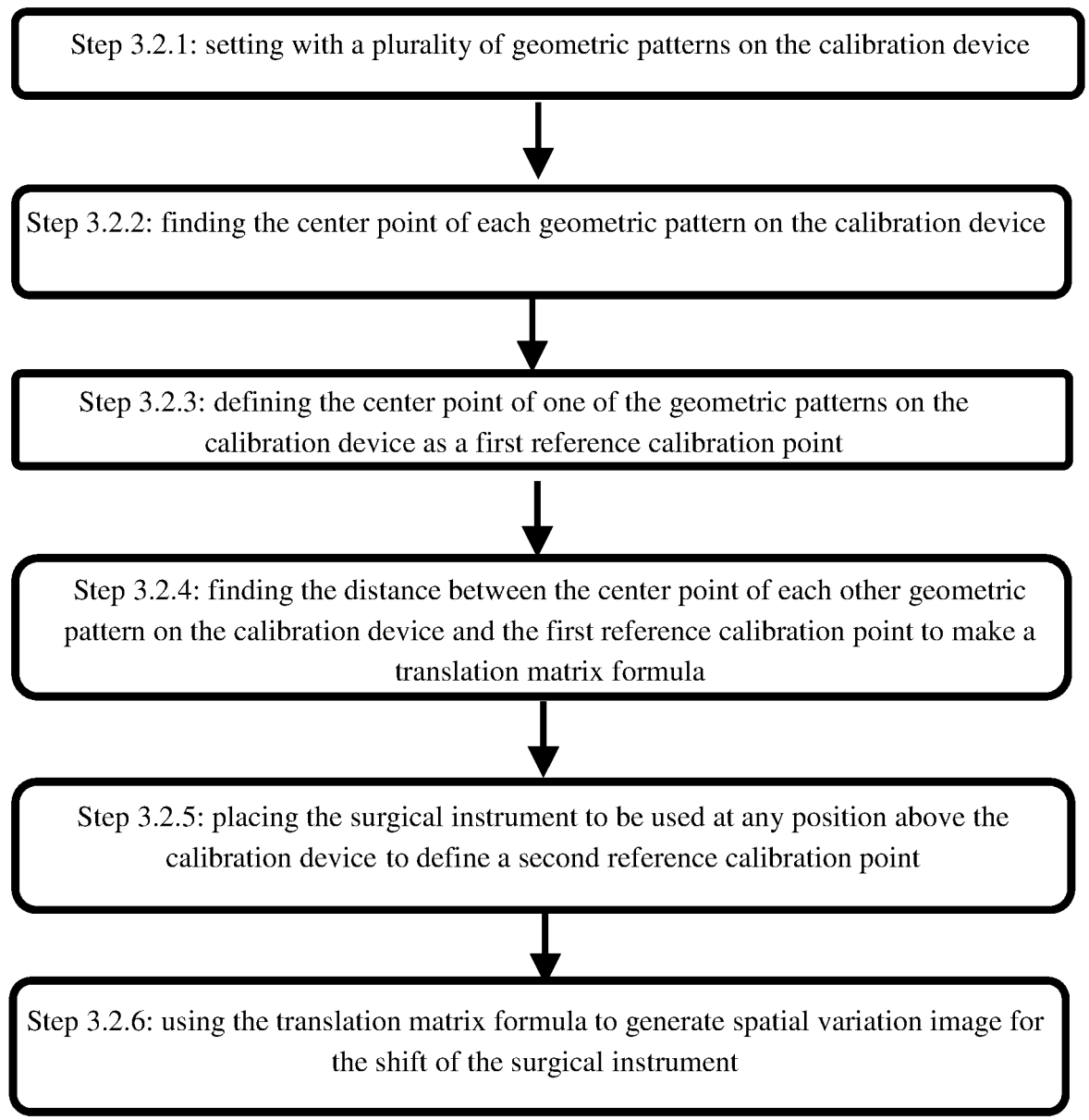
FIG. 5 is a procedure flowchart of another embodiment of the object developing and calibrating method of the present invention.

FIG. 5 shows a procedure flowchart of another embodiment of the object developing and calibrating method of the present invention. And please also refer to FIG. 2. The step 3.2 comprises the following steps:

Step 3.2.1: setting with a plurality of geometric patterns 110 or 120 on the calibration device 100;

Step 3.2.2: finding the center point of each geometric pattern 110 or 120 on the calibration device 100;

Step 3.2.3: defining the center point of one of the geometric patterns 110 or 120 on the calibration device 100 as a first reference calibration point;

Step 3.2.4: by using the first reference calibration point as a positioning reference point, finding the distance between the center point of each other geometric pattern 110 or 120 on the calibration device 100 and the first reference calibration point to make a translation matrix formula;

Step 3.2.5: placing the surgical instrument 200 to be used at any position above the calibration device to define a second reference calibration point;

Step 3.2.6: using the translation matrix formula to generate spatial variation image for the shift of the surgical instrument.

In an embodiment, all the geometric patterns are the same. In an embodiment, the geometric patterns have a distance 112, 122 between 0.2 mm and 0.5 mm. In a preferred embodiment, the geometric patterns have a distance between 0.3 mm and 0.4 mm to have accurate calibration.

In an embodiment, in step 3.2.4, the translation matrix formula is obtained from the positional characteristics of the center point of each geometric pattern detected by a function library and then performed by a mathematical operation. The translation matrix formula is obtained in detail from linking a first conversion matrix and a second conversion matrix. The first conversion matrix is obtained by relating the infrared LED 20 on the surgical eyeglass 10 and the center point of each geometric pattern 110 or 120 on the calibration device 100. The second conversion matrix is obtained by relating the eye of the doctor and the infrared LED 20. And the translation matrix formula which is related to the eyes of the doctor and the each geometric pattern 110 or 120, is then obtained by linking the first conversion matrix and the second conversion matrix.

Obtaining the first conversion matrix uses a first library to detect the position feature of the marked point and uses a first mathematical operation for the position feature of the each geometric pattern 110 or 120 on the calibration device 100 to obtain the first conversion matrix. Obtaining the second conversion matrix of the eye of the doctor and the infrared LED 20 use a second library to obtain a three-dimensional coordinate corresponding to the infrared LED 20, to obtain the second conversion matrix of two-dimensional coordinate and the infrared LED 20 by a second mathematical operation, and use a de-coupling equation to obtain the second conversion matrix. The value of the first conversion matrix of the infrared LED 20 and the each geometric pattern 110 or 120 on the calibration device 100 is varied, but can be obtained by the infrared LED 20; the value of the second conversion matrix of the eyes of the doctor and the infrared LED 20 is fixed, but the value is unknown. The value of the translation matrix formula is variable and unknown, and can be obtained by multiplying the first conversion matrix by the second conversion matrix.

The translation matrix formula is from a three-dimensional model of the component library constructed. The function library uses OOOPDS rendering core algorithm, to construct the bounding box using the three-dimensional model component library; to implement collision detection; to calculate component libraries, to implement force feedback and serial communication using the data communication component library function console such as 802.11g, TCP/IP or RS232, etc. In an embodiment, the function library is an OOOPDS library written in C/C++ language.

In an embodiment, in Step 3.2.6: using the translation matrix formula to generate spatial variation image for the shift of the surgical instrument.

In an embodiment, the surgical site image required to be used in other surgical procedures is selected from one of the following: computer tomography imaging (CT), magnetic resonance imaging (MRI), X-ray imaging, positive medical imaging and nuclear medical imaging.

The image overlay software is implemented by the processing device 300 with an associated display. The processing device 300 operates the image overlay software for processing images and data, and for communicating images and data via wired or wireless connections. For example, the image overlay software can be used by the medical clinician images to manipulate, convert, and overlay images collected by the surgical site image required to be used in other surgical procedures. Although different machines may produce images in different formats, it is desirable that image overlay software be capable of converting one or more image formats into one or more different formats, so that the images collected by different devices can be displayed together in an overlying fashion. Thus, the image overlay software is configured to access, display, convert, and manipulate a new spatial change image by combining the spatial variation image with the image of the surgical site to be used in other surgical procedures in various formats including, for example, DICOM images, CAD images, STL images, or the like. The image overlay software permits a clinician to review digital images, visualize virtual models and create image overlays on display of the surgical eyeglass worn by a surgeon.

In an embodiment, the new spatial variation image is inputted into a surgical eyeglass worn by a surgeon. The surgeon, by means of the surgical eyeglass, defines the working depth for the entire optical system on the surgical eyeglass and, by moving his head, automatically, illuminates the operating area by pointing the headlight according to head movement. Thus the image which is returned from the surgical site is always directed along the same line as the illumination pattern. The surgeon, by moving his head, automatically aims the headlight, and the eyes of the surgeon perceive the area illuminated by the beam which then, based on the orientation of the optical system on the surgical eyeglass, produces an image which essentially is completely indicative of exactly what the surgeon is seeing.

According to the disclosure, the present invention provides an object developing and calibrating method that can solve the problem of the interference of non-surgical environmental imaging noises in the surgical environment, such as operating table, or drop rack, and thus help the surgeon see the object images that the surgeon intends to look at on the surgical eyeglass, such as the images of surgical instruments, affected areas, etc.

While the invention has been disclosed in the foregoing preferred embodiments, they are not intended to limit the present invention, and one skilled in the art, without departing from the spirit and scope of the present disclosure, may make various changes or modifications. Therefore, the scope of the present invention is best defined by the appended claims.

What is claim is:

1. An object developing and calibrating method in a surgical environment, comprising the steps of:
    Step 1: disposing at least one infrared LED (IR-LED) and at least one infrared sensor (IR-Sensor) on a surgical eyeglass, the IR-LED emitting an infrared signal to illuminate a plurality of objects in the surgical environment, and the IR-Sensor receiving the infrared signal reflected by the plurality of objects to form an object image of the surgical environment;
    Step 2: transmitting the object image of the surgical environment to an image processing module of a processing device;
    Step 3: forming a spatial variation image for a displacement of a surgical instrument by the at least one IR-LED and the at least one IR-Sensor on the surgical eyeglass;
    Step 4: transmitting the spatial variation image to the image processing module of the processing device to overlap with the object image of the surgical environment to form a surgical environment image; and
    Step 5: with the image processing module of the processing device, retaining image signals within a first wavelength range in the surgical environment image and removing image signals not in the first wavelength range;
    wherein the Step 3 comprises the steps of:
        Step 3.1: emitting an infrared signal from the IR-LED on the surgical eyeglass to illuminate a calibration device and the surgical instrument, wherein the calibration device has thereon a plurality of geometric patterns and a reflective IR coating outside the geometric patterns, and a specific point on the surgical instrument has a reflective IR coating, to reflect the infrared signal; and
        Step 3.2: receiving the infrared signal reflected by the reflective IR coating on the calibration device and the surgical instrument by the IR-Sensor on the surgical eyeglass and then transmitting the reflected infrared signal to the image processing module of the processing device to form a spatial variation image.

2. The object developing and calibrating method according to claim 1, wherein the image processing module of the processing device has an optical filter.

3. The object developing and calibrating method according to claim 1, wherein the step 3.2 comprises the steps of:
    Step 3.2.1: setting with a plurality of geometric patterns on the calibration device;
    Step 3.2.2: finding the center point of each of the geometric patterns on the calibration device;
    Step 3.2.3: defining the center point of one of the geometric patterns on the calibration device as a first reference calibration point;
    Step 3.2.4: by using the first reference calibration point as a positioning reference point, finding the distance between the center point of each of the other geometric patterns on the calibration device and the first reference calibration point to make a translation matrix formula;
    Step 3.2.5: placing the surgical instrument to be used at any position above the calibration device to define a second reference calibration point; and
    Step 3.2.6: using the translation matrix formula to generate the spatial variation image for the shift of the surgical instrument.

4. The object developing and calibrating method according to claim 3, wherein the geometric patterns are selected from circular patterns or triangular patterns.

5. The object developing and calibrating method according to claim 3, wherein the distance of adjacent geometric patterns is between 0.2 mm and 0.5 mm.

6. The object developing and calibrating method according to claim 1, wherein the reflective IR coating is made with pigments and an organic or inorganic vehicle.

7. The object developing and calibrating method according to claim 1, wherein the infrared signal emitted by the at least one IR-LED has a wavelength in the range of 750 nm to 1100 nm.

8. The object developing and calibrating method according to claim 1, wherein the infrared signal received by the at least one IR-Sensor has a wavelength in the range of 750 nm to 1100 nm.

9. The object developing and calibrating method according to claim 1, wherein the first wavelength range is from 750 nm to 1100 nm.

10. The object developing and calibrating method according to claim 1, wherein in Step 4, the spatial variation image and the object image of the surgical environment are overlapped by an image overlay software in the image processing module of the processing device.

* * * * *